US006838673B2

(12) United States Patent
Morishita (10) Patent No.: US 6,838,673 B2
(45) Date of Patent: Jan. 4, 2005

(54) ELECTROMAGNETIC WAVE TRANSFORMING DEVICE

(75) Inventor: Masakazu Morishita, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 85 days.

(21) Appl. No.: 09/984,174

(22) Filed: Oct. 29, 2001

(65) Prior Publication Data

US 2002/0066861 A1 Jun. 6, 2002

(30) Foreign Application Priority Data

Nov. 1, 2000 (JP) ........................................ 2000-335004

(51) Int. Cl.⁷ ................................................ H04N 5/32
(52) U.S. Cl. ............................. 250/370.09; 250/370.11
(58) Field of Search ...................... 250/370.09, 370.11, 250/370.14, 208.1, 208.2, 208.3, 338.4; 345/77

(56) References Cited

U.S. PATENT DOCUMENTS

| 5,084,747 A | * | 1/1992 | Miyawaki | 257/432 |
| 5,319,206 A | | 6/1994 | Lee et al. | 250/370.09 |
| 5,812,191 A | * | 9/1998 | Orava et al. | 348/308 |
| 5,856,686 A | * | 1/1999 | Watanabe et al. | 257/291 |
| 5,965,872 A | | 10/1999 | Endo et al. | 250/208.1 |
| 6,323,490 B1 | * | 11/2001 | Ikeda et al. | 250/370.09 |
| 6,330,303 B1 | * | 12/2001 | Yamane et al. | 378/98.8 |
| 6,424,326 B2 | * | 7/2002 | Yamazaki et al. | 345/77 |
| 6,429,436 B1 | * | 8/2002 | Tomisaki et al. | 250/370.09 |
| 6,489,618 B1 | * | 12/2002 | Morishita | 250/370.09 |
| 6,538,253 B2 | * | 3/2003 | Petrick et al. | 250/370.09 |
| 6,583,456 B2 | * | 6/2003 | Haga et al. | 257/292 |
| 6,600,160 B2 | | 7/2003 | Kobayashi et al. | 250/370.14 |

FOREIGN PATENT DOCUMENTS

| EP | 1 207 560 A2 | 5/2002 |
| JP | 05-207376 | 8/1993 |
| JP | 07-171142 | 7/1995 |
| JP | 11-183626 | 7/1999 |
| JP | 11-307756 | 11/1999 |

OTHER PUBLICATIONS

U.S. Appl. No. 09/985,534 filed Nov. 5, 2002, Morishita.
U.S. Appl. No. 09/816,360 filed Mar. 26, 2002, Morishita.

* cited by examiner

Primary Examiner—Constantine Hannaher
Assistant Examiner—Otilia Gabor
(74) Attorney, Agent, or Firm—Fitzpatrick, Cella, Harper & Scinto (57) ABSTRACT

An electromagnetic wave detecting device is provided, which comprises: a detecting unit for transforming an electromagnetic wave into an electric charge for detection, a reset unit for resetting the potential of the detecting unit, a storing unit for storing a signal electric charge generated in the detecting unit by the electromagnetic wave, a first reading unit for reading the signal electric charge, and a second reading unit for reading the potential of the signal electric charge stored in the storing unit in a nondestructive manner.

15 Claims, 10 Drawing Sheets

FIG. 12B
PRIOR ART

ELECTROMAGNETIC WAVE TRANSFORMING DEVICE

BACKGROUND OF THE INVENTION

1. Field of the Invention

The present invention relates to an electromagnetic wave transforming device for transforming an electromagnetic wave represented by high energy radiant rays such as X-rays or γ-rays or radiant rays such as α-rays into electric signals.

2. Related Background Art

Up to now, the electromagnetic wave transforming device using X-rays among electromagnetic waves represented by high energy radiant rays such as X-rays or γ-rays, α-rays or β-rays has an imaging device portion for image input and a detecting device portion that detects the irradiation quantity of X-rays, separately, those portions being connected as independent devices in use.

In the above structure, the X-ray quantity in the imaging device is controlled on the basis of the X-ray irradiation quantity detected by the detecting device.

In this situation, in the case where a detecting element for detecting the X-ray quantity is located in front of the imaging device portion of the X-ray imaging device to detect the X-rays, there is a case in which an image obtained by the imaging device is adversely affected by the detecting element.

Subsequently, an example of a conventional X-ray automatic exposure control device will be described.

The automatic exposure control device (photo timer) in the X-ray photographing is used in most of indirect photographing and direct photographing and widely spread.

The automatic exposure control device operates so as to hold the X-ray quantity irradiated onto a film to a desired range by automatically controlling a photographing time. The X-rays that have passed through an object to be photographed is transformed into an electric signal, and when an integral value of the electric signals reaches a given value, the X-rays are blocked (or the irradiation of the X-rays stops) so as to obtain a desired film density.

The automatic exposure control devices are classified into various types in accordance with the X-ray detecting mechanism and a control mechanism such as a method of determining the X-ray exposure conditions.

Figure 11:
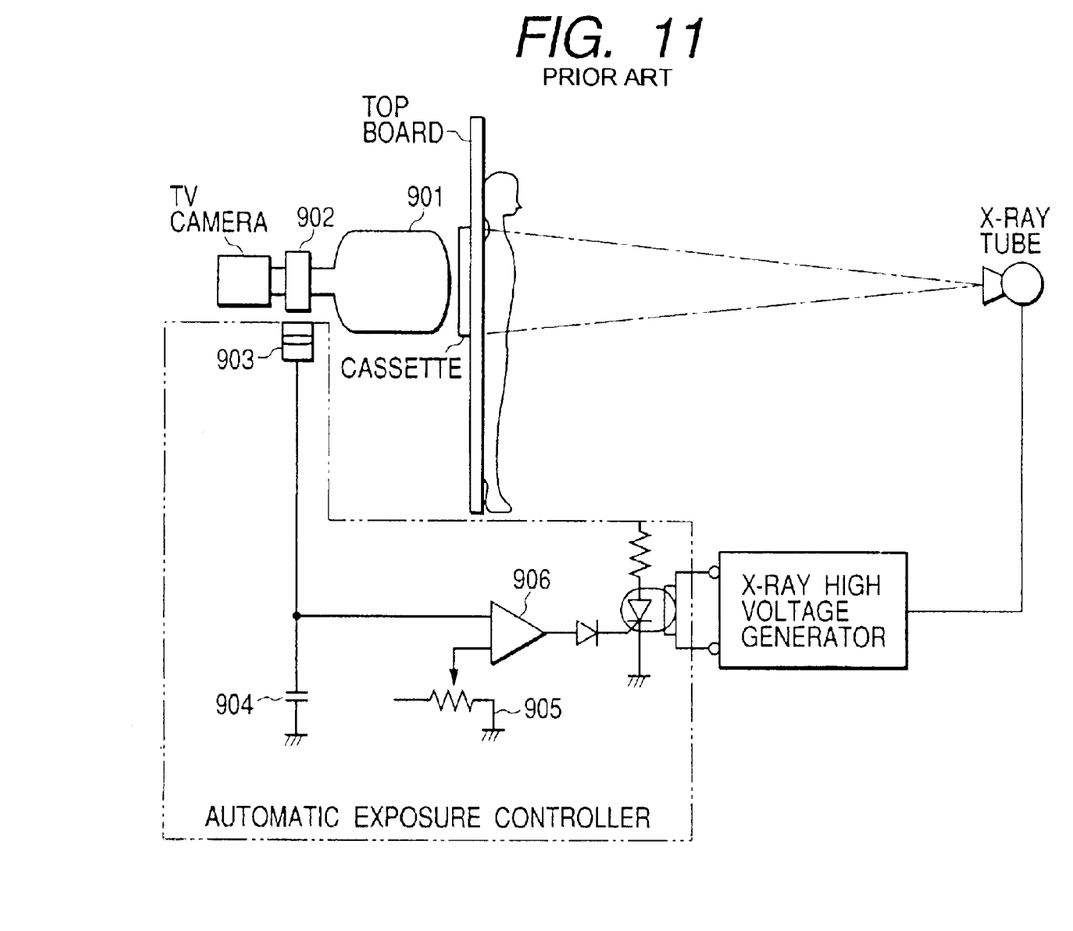
FIG. 11 is a conceptual diagram showing the structure of an automatic exposure control device in a conventional example.

An example of the structure of the automatic exposure control in a transmission fast photographing is shown in FIG. 11.

In the figure, the X-rays that have passed through an object to be photographed is converted and amplified into a visible light by I.I. (image intensifier) 901. A part of the output light of the I.I. 901 is guided to a photoelectron multiplexing tube 903 through a distributor 902 and then transformed into an electric signal. The electric signal is integrated by a capacitor 904. The integral value corresponds to the degree of exposure of the film and is compared with a reference value set by a film density setter 905 by a comparator 906, and when the integral value reaches the set value, an X-ray block signal is generated to stop the irradiation of the X-rays.

Subsequently, a conventional detector will be described.

As means for detecting the X-ray that has passed through the object to be photographed, there are an I.I. natural lighting type, a cassette front face fluorescent lighting type, a cassette rear face fluorescent lighting type, an ionization box type and a semiconductor detection type that is being now studied. Those types can be roughly classified into the front face natural lighting system and the rear face natural lighting system.

Both of the cassette front face fluorescent lighting type and the ionization box type are of the (cassette) front face natural lighting system in which a detector is disposed between a film and an object to be photographed.

The I.I. natural lighting type and the cassette rear face fluorescent lighting type are of the rear face natural lighting system in which the X-rays that have passed through the film is detected.

Figure 12A:
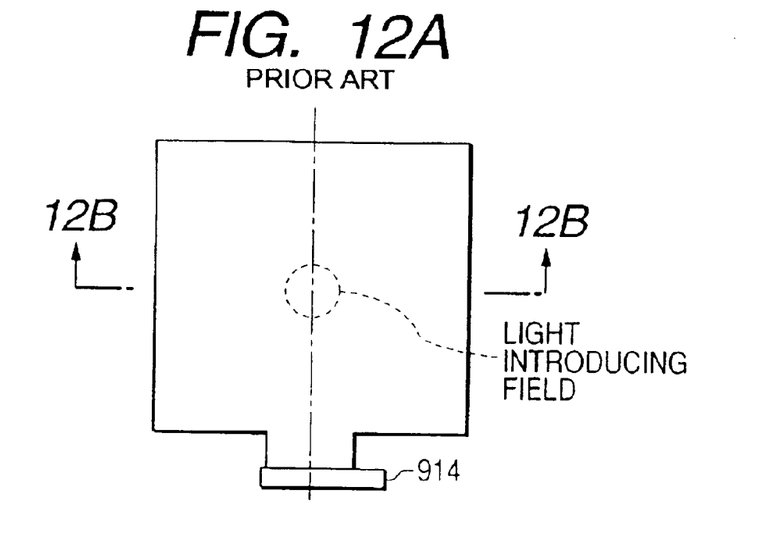
FIGS. 12A and 12B are diagrams showing an example of a fluorescent lighting type detector used in the automatic exposure control device shown in FIG. 11.
Figure 12B:
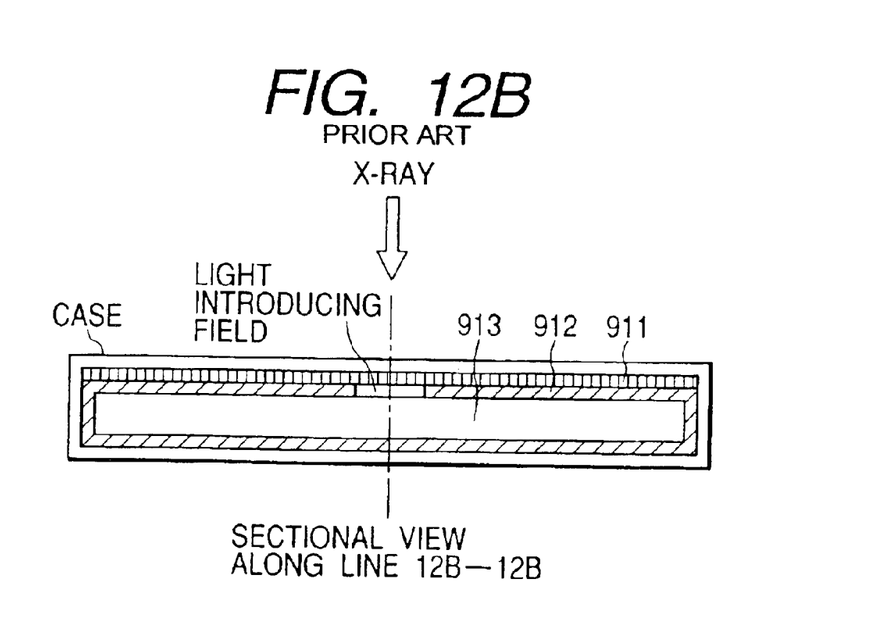

FIGS. 12A and 12B show an example of a fluorescent lighting type detector in which the thickness of the detector is about 2.5 mm which is significantly thinner than that of the ionization box (the thickness of about 10 mm). The detecting mechanism of the fluorescent lighting type is that the X-rays that have passed through the object to be photographed are applied to a fluorescent paper (phosphor) 911 to fluoresce the phosphor. Then, the fluorescence in a hollowed portion of a light block paper 912 is guided to a light guide plate 913, and reaches the photoelectron multiplexing tube 914 so as to be inputted to the photoelectron multiplexing tube 914 to conduct photoelectric conversion.

As described above, in the case where the X-ray amount detecting element is disposed in front of the X-ray imaging device to detect the X-rays, because the detecting element receives a part of image information before the electromagnetic waves such as the X-rays reach an imaging region, obtained image information may be adversely affected.

Also, the cassette front face natural lighting system is more influenced by the X-ray absorption and scattering rays due to the exposure quantity detection than the rear face natural lighting system, as a result of which the image quality may be deteriorated, or the exposure quantity may increase in order to supplement the absorption. As the thickness of the detector is thicker, a distance between the object to be photographed and the film becomes longer with the result that geometrical blur becomes large, to thereby deteriorate the image quality. This is because the X-ray tube focal point is displaced from the image receiving position of a film or a sensor which is an imaging section because of the thickness of the detector.

In addition, in case of the rear face natural lighting system, the X-ray absorption between the X-ray source that makes the film photosensitive and the detector is normally large, and there are many cases in which the tube voltage dependency characteristic is deteriorated. Also, when the rear face absorption is reduced in order to reduce the tube voltage dependency characteristic, the film is liable to be adversely affected by the backward scattering rays generated when the X-rays that have passed through the film are irradiated onto a backward member.

SUMMARY OF THE INVENTION

The present invention has been made in order to solve the above-mentioned problems with the conventional device.

Another object of the present invention is to provide an electromagnetic transforming device which is capable of detecting the irradiation quantity of electromagnetic waves such as X-rays and is capable of transforming image information of the electromagnetic wave into an electric signal. That is, an imaging portion and a portion of detecting the X-ray irradiation quantity are integrated together, thereby being capable of downsizing the device.

Still another object of the present invention is to provide an electromagnetic wave transforming device which is capable of detecting the irradiation quantity of the electromagnetic wave by the electromagnetic wave transforming device per se and is capable of accurately detecting the irradiation quantity.

Yet still another object of the present invention is to provide an electromagnetic wave transforming device which is capable of detecting the irradiation quantity of the electromagnetic wave at a plurality of portions and is capable of detecting the irradiation quantity of the X-rays without any influence on the pick-up image.

The present invention is made to solve at least one of the above-mentioned problems.

The present invention has been made to solve at least one of the above-mentioned problems, and is achieved by providing an electromagnetic wave detecting device including detecting means for transforming an electromagnetic wave into an electric charge for detection, reset means for resetting the potential of the detecting means, storing means for storing a signal electric charge generated in the detecting means by the electromagnetic wave, first reading means for reading the signal electric charge, and second reading means for reading the potential of the signal electric charge stored in the storing means in a nondestructive manner.

Further, in the device, a sensor having the detecting means, the reset means, the storing means and the first reading means may be arranged on a substrate in a matrix.

Further, in the device, the second reading means may include means for discriminating the potentials of the signal electric charges of a plurality of sensor cells to obtain a specific potential, whereby the detected voltage of an appropriately optimum group can be used in accordance with an imaging portion of an object to be photographed, which is referable.

Further, in the device, the reset means, the storing means and the first and second reading means may be formed on a thin film transistor formed on an insulating substrate, respectively.

Further, in the device, one terminal of the detecting means may be connected with a potential supply means, and the other terminal of the detecting means may be connected with a source or a drain of the transistors of the reset means and the reading means and a gate of the transistor of the storing means.

Further, the device may include means for holding a voltage at the other terminal of the detecting means constant.

Further, the device may include a source follower circuit that reads the gate potential of the transistor of the storing means to detect the stored electric charge.

Further, in the device, the detecting means may include an x-ray sensing section in which a metal layer, an i layer and a metal layer are directly stacked one on another.

Further, in the device, a semiconductor that forms the thin film transistor may be made of non-single crystal silicon.

Further, in the device, the detecting means may include a first substrate of semiconductor crystal that directly transforms the electromagnetic wave into the electric charge, the other means may be formed on a second insulating substrate or a semiconductor substrate, the first substrate and the second substrate may be stacked one on another, and the sensor cell of the first substrate and the reading circuit of the second substrate may be electrically and mechanically connected to each other by a laminate structure of the first and second substrates.

Further, an electromagnetic wave detecting system is provided by including, means for transforming an electromagnetic wave into an electric charge, means for resetting the potential of the detecting means, means for storing a signal electric charge generated in the detecting means by the electromagnetic wave, reading means for reading the signal electric charge stored in the storing means, means for reading a potential of the signal electric charge stored in the storing means in a nondestructive manner to detect an irradiation integral quantity of the electromagnetic wave, and control means for comparing the irradiation integral quantity with a predetermined value to stop the irradiation of the electromagnetic wave, whereby being capable of preventing an excessive irradiation of radiant rays to a human body, for example, in an X-ray photographing device, which is preferable.

The details will be described with reference to embodiments that will be described later.

DESCRIPTION OF THE PREFERRED EMBODIMENTS

Now, a description will be given in more detail of preferred embodiments of the present invention with reference to the accompanying drawings.

(First Embodiment)

Figure 1A:
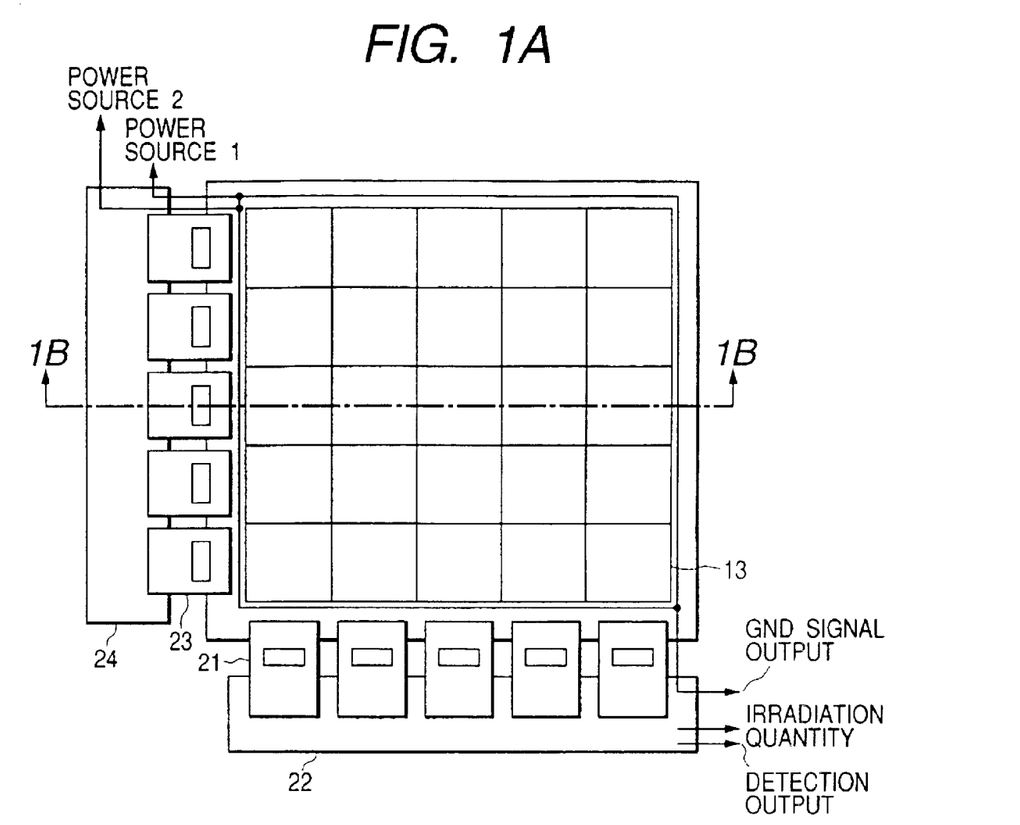
FIG. 1A is a partial plan view showing an electromagnetic wave transforming device in accordance with an embodiment of the present invention.
Figure 1B:
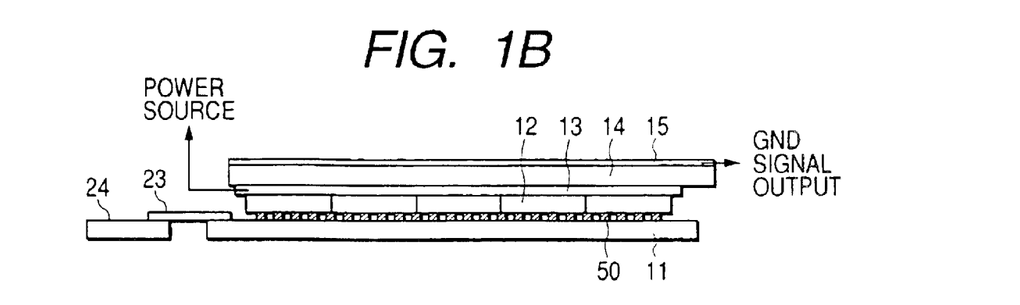
FIG. 1B is a cross-sectional view showing the electromagnetic wave transforming device in accordance with the embodiment of the present invention.

FIGS. 1A and 1B show the structure of an electromagnetic wave transforming device in accordance with a first embodiment of the present invention, in which FIG. 1A is a plan view thereof, and FIG. 1B is a cross-sectional view taken along a line 1B—1B.

Reference numeral 11 represents a substrate where thin film transistors, capacitors and so on are formed on an insulating (glass) substrate, and the thin film transistors and the capacitors are arranged in a two-dimensional matrix.

Reference 12 denotes a semiconductor substrate having a semiconductor that directly detects a high energy radiant ray, and made of GaAs, CdTe or the like as the semiconductor.

The substrate 11 and the semiconductor substrate 12 are coupled to each other vertically for each of cells with a conductor 50.

Reference numeral 13 denotes one conductor for commonly biasing a plurality of semiconductor substrates 12. The conductor 13 may be formed in a sheet shape or a mesh shape.

Reference numeral 14 denotes an insulating sheet, and 15 is a bias shield sheet. As usual, since a voltage of 100 V or higher is applied to the conductor 13, the insulating sheet 14 and a bias shield sheet 15 function as its protection. The insulating sheet 14 may be an air gap. In this case, a bias shield sheet is disposed between the insulating sheet 14 and the housing of the detector.

Reference numeral 21 is a tape carrier package (TCP) of a signal processing IC for obtaining a signal output from the detector, and reference numeral 22 is a printed board of the signal processing circuit.

Reference numeral 23 denotes a TCP of the driver IC, and 24 is a driver printed board.

Figure 2:
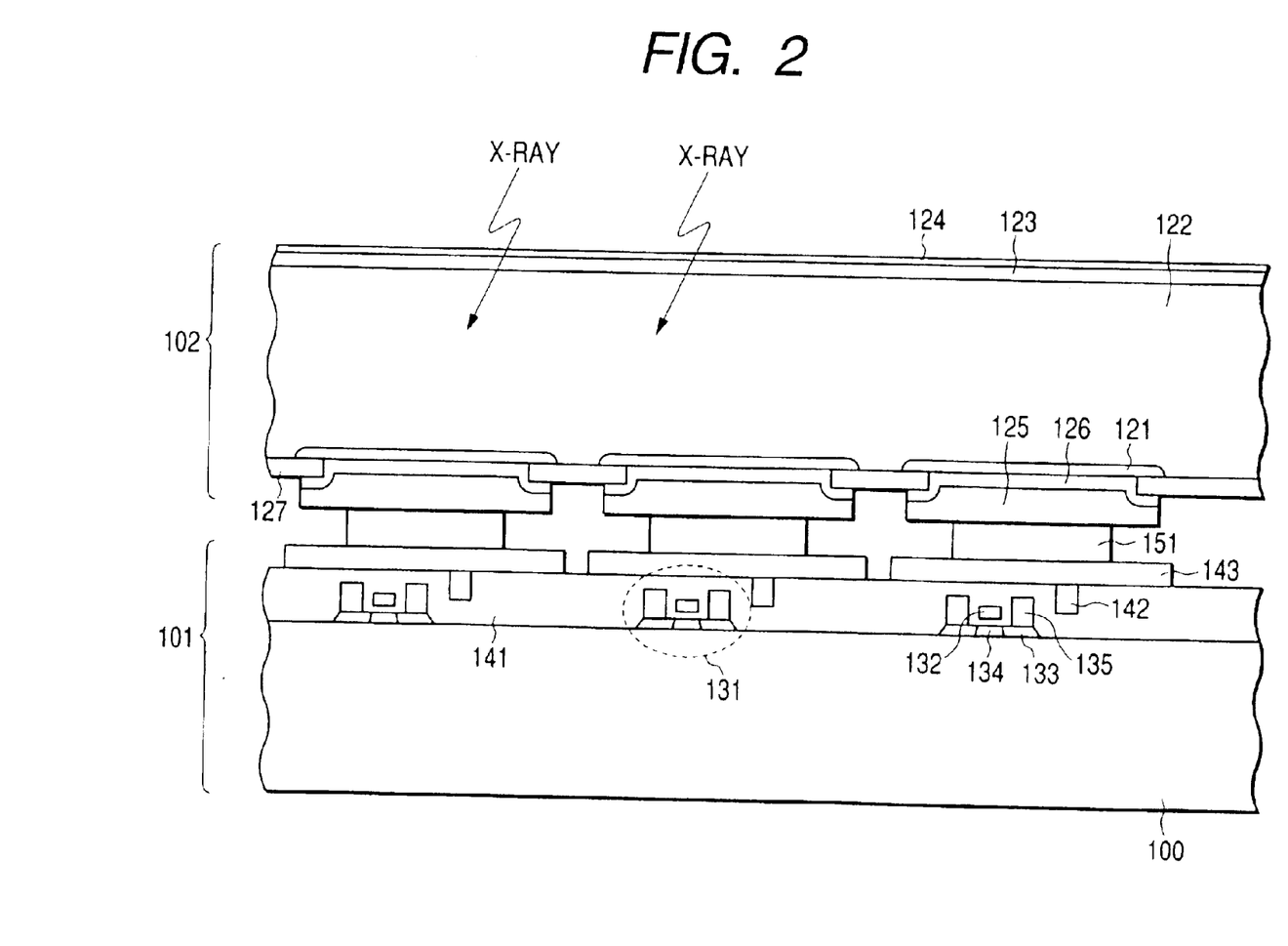
FIG. 2 is a partial cross-sectional view showing an electromagnetic wave transforming device in accordance with a first embodiment of the present invention.

FIG. 2 is a cross-sectional view showing the X-ray sensor in accordance with the embodiment.

Reference numeral 102 is an X-ray sensing section that produces electrons and positive holes from the X-rays and stores and reads one carrier of the electrons and the positive holes. Reference numeral 101 is a carrier read section in which thin film transistors, capacitors and so on are formed on the insulating substrate 100.

The X-ray sensing section 102 is made of a semiconductor such as GaAs, GaP, Ge or CdTe, which includes an n+ layer 121 with the n-type high impurity density of $10^{18}$ cm$^{-3}$ or more, an i layer 122 and a p+ layer 123 with the p-type high impurity density of $10^{18}$ cm$^{-3}$ or more. A depletion layer is made up of a pin diode that spreads from an interface between the n+ layer 121 and the i layer 122, a metal layer 124 formed on the p+ layer 123, and metal layers 125 and 126 formed under the n+ layer 121. The metal layer 126 is an ohmic contact metal. Reference numeral 127 is a protective layer such as SiN. The metal layer 125 is set to about 1 to 10 μm in height by plating a material such as Au in order to ease the connection of the upper and lower substrates.

The i layer is directed to a high resistant layer of the semiconductor. Also, the metal layer 124 is made of, for example, AuZn, and the metal layer 126 is made of, for example, AuGeNi.

The carrier reading section 101 has a thin film transistor (hereinafter referred to as "TFT") 131 which constitutes a circuit on the insulating substrate 100, and the TFT 131 is formed of a gate 132, a drain 133, an active layer 134, and a metal wiring 135 connected to the source and the drain. The TFT 131 is covered with a protective film 141. Reference numeral 142 is an Al layer, and 143 is a metal layer. The carrier reading section 101 also has a capacitor although it is not shown in FIG. 2.

The metal layer 143 of the carrier reading section 101 and the metal layer 125 of the X-ray sensing section 102 are connected by a connection member 151 made of a metal or an electroconductive adhesive.

Figure 3:
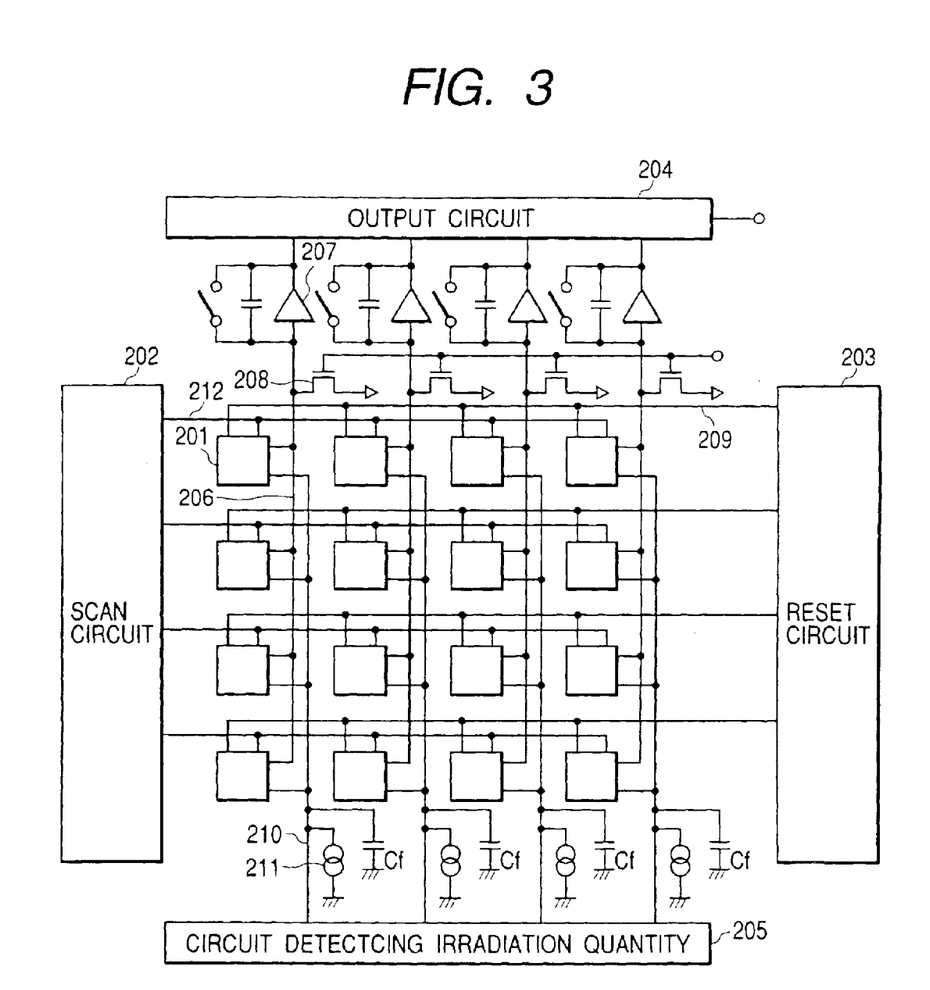
FIG. 3 is a circuit diagram showing the entire electromagnetic wave transforming device in accordance with the first embodiment of the present invention.

FIG. 3 shows an equivalent circuit of the electromagnetic wave converting device shown in FIGS. 1A and 1B and FIG. 2. A sensor cell 201 is arranged two-dimensionally. A scanning circuit 202 and a reset circuit 203 are arranged beside the horizontal direction of the sensor cell 201. The scanning circuit 202 and the reset circuit 203 may be disposed in a driver circuit mounted on a drive printed board 24 shown in FIGS. 1A and 1B. In addition, the reset circuit 203 has an output circuit 204 and an irradiation quantity detecting circuit 205.

A transistor of the respective sensor cells 201 is selected for each row by the scanning circuit 202, and a signal is read from the respective sensor cells 201 to an output line 206, and signals from the respective sensor cells 201 are sequentially outputted through an amplifier 207 connected to the output line 206 by the output circuit 204 for each of columns. The output line 206 is reset to a constant potential by a reset transistor 208. The respective sensor cells 201 are reset through the respective reset lines 209 from the reset circuit 203 for each of rows.

The irradiation quantity detecting circuit 205 detects the highest potential of the sensor cell 201 of each column in a non-destructive manner through the output line 210 that is common for each of columns. Reference numeral 211 is a constant current source.

Figure 4:
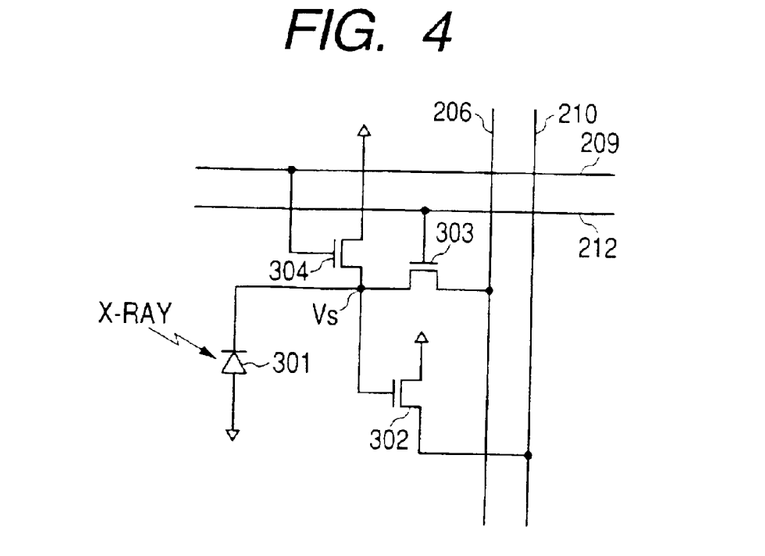
FIG. 4 is an equivalent circuit diagram showing the respective sensor cells in the electromagnetic wave transforming device in accordance with the first embodiment of the present invention.
Figure 5:
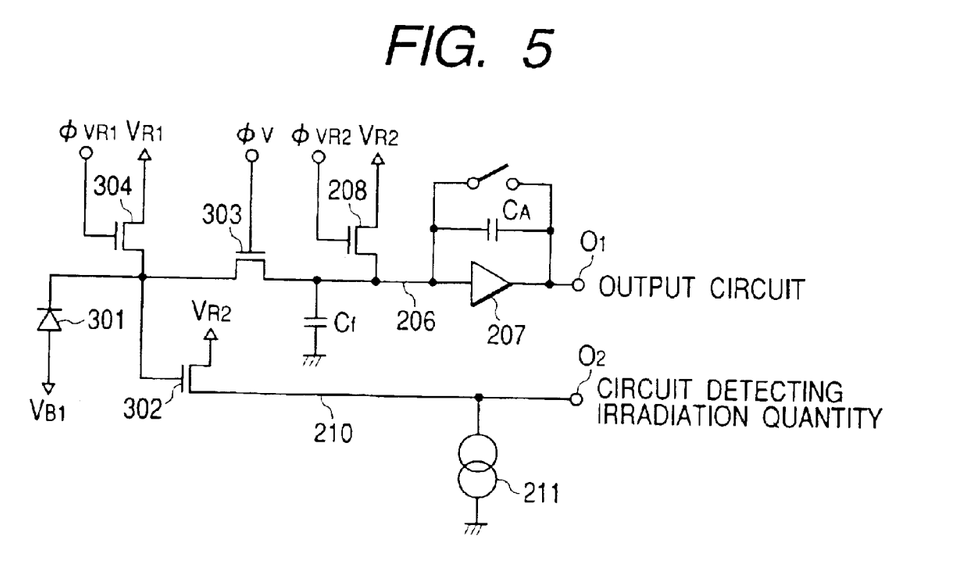
FIG. 5 is an equivalent circuit diagram showing a sensor cell, a read circuit and so on when attention is paid to one sensor cell of the electromagnetic wave transforming device in accordance with the first embodiment of the present invention.

FIG. 4 shows an equivalent circuit of the respective sensor cells 201, and FIG. 5 shows a sensor cell 201 and an equivalent circuit upstream of an output.

The sensor cell 201 includes an X-ray sensing section 301 that transforms the X-ray into a signal electric charge, a non-destructive read and signal electric charge storing transistor 302 (hereinafter simply referred to as "transistor 302") which stores the signal electric charge in the gate and reads its potential in a non-destructive manner, a destructive read transistor 303 (hereinafter simply referred to as "transistor 303") which reads the signal electric charge from the respective sensor cells 201, and a reset transistor 304 for completely resetting the signal electric charge (hereinafter simply referred to as "transistor 304").

The capacitance C in which a signal charge Q generated in the X-ray sensing section 301 is stored in the X-ray sensing section 301 by X-ray input is determined by the sum $\Sigma Cn$ of the gate capacitance C2 of the transistor 302, the capacitances C3 and C4 of the transistors 303 and 304 viewed from the gate of the transistors 302, and the capacitance C1 of the X-ray sensing section 301, and a signal voltage appearing in the gate of the transistor 302 becomes $Vs=Q/\Sigma Cn$. The signal voltage is obtained to an output line 210 as an output of a source follower (made up of the transistor 302 and the constant current source 211) by the transistor 302.

In FIG. 5, the capacitance Cf is a floating capacitance occurring in the output line 206. The capacitance Cf is formed of the capacitances at the cross sections of the row select lines 212 which are lateral wirings and reset lines 209, the capacitance of the source (drain) of the transistor 303 and so on. In a large-sized panel, the capacitance becomes large, which largely influences the signal (S) to noise (N) ratio (S/N) of the sensor. In a single crystal substrate, a floating capacitance is formed between the wiring and the substrate, which is added to the capacitance of the cross section and the source section. In the insulating substrate, since the capacitance between the wiring and the substrate disappears, it is more preferable than the single crystal substrate in the large-sized area sensor of 10 cm² or more. In the amplifier 207 of FIG. 5, since the noise Nin of the amplifier becomes 1+Cf/Ca times, Cf is preferably smaller. The CA is a capacitance for integration which is connected between the input and output of the amplifier 207.

The above signal voltage Vs becomes the voltage of Vs to Vth to the source of the transistor 302 and is then outputted to an output terminal O2 connected to the irradiation quantity detecting circuit 205. Vth is a source to gate voltage of the transistor. Also, the output from the respective sensor cells 201 is outputted to the output terminal O1 connected to the output circuit 204 through the amplifier 207 from the transistor 303.

Figure 6:
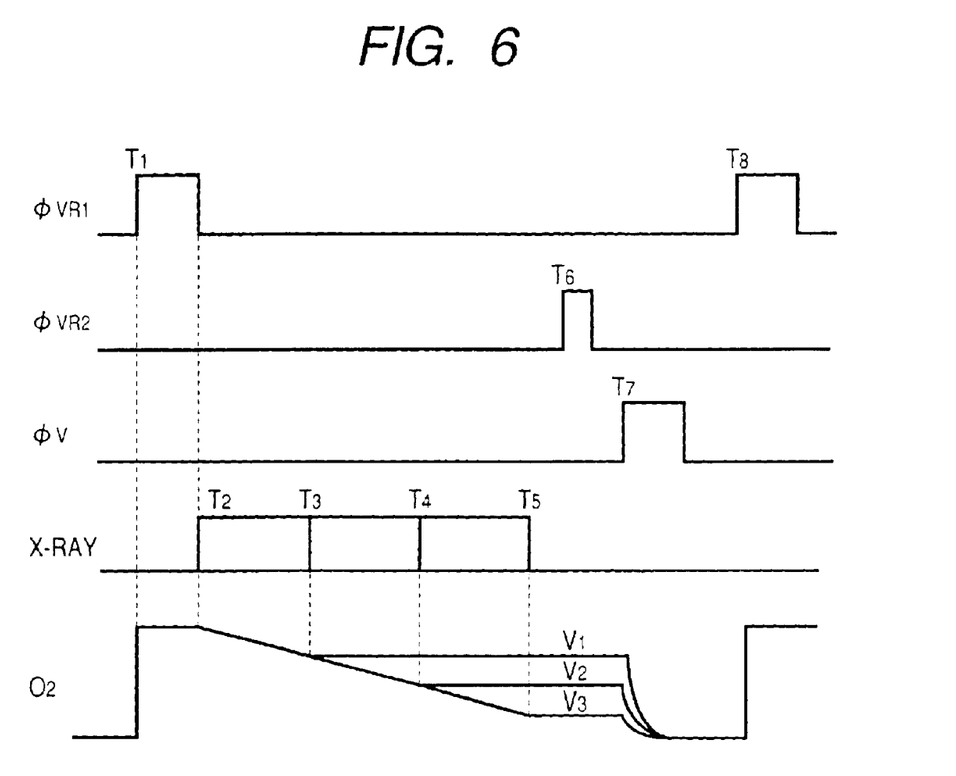
FIG. 6 is a timing chart showing the operation of the electromagnetic wave transforming device in accordance with the embodiment of the present invention.

FIG. 6 is a timing chart for explanation of the operation.

In the figure, ΦVR1 is a reset signal of the sensor cell 201, ΦVR2 is a reset signal of the output line 206, Φv by is a read control signal for conducting read from the sensor cell 201 to the output line 206, the X-ray is an X-ray input timing, and O2 is an output potential to the irradiation quantity detecting circuit 205. Similarly, in FIG. 4. ΦVR1, ΦVR2, Φv and O2 to which the respective signals are given are shown.

Initially, at a time T1, when the potential of the sensor cell 201 is made a constant value by the reset signal ΦVR1, the potential of the output terminal 02 is set to a predetermined voltage. At a time T2, when the reset signal ΦVR1 is reset, the potential of the output terminal O2 changes due to the signal electric charge generated by the X-ray detection in the sensor cell 201. The potential of the output terminal 02 becomes voltages V1, V2 and V3 at times T3, T4 and T5, respectively. The X-ray generator is controlled to adjust the X-ray exposure time by using an external circuit using an output from the irradiation quantity detecting circuit 205 which is applied with a voltage of the output terminal O2, changes over, amplifies and outputs that voltage. This is an automatic exposure function.

In an example of FIG. 6, at a time T5, when the voltage at the output terminal O2 becomes V3, the X-ray irradiation is suspended by the automatic exposure function.

At a time T6, after the potential of the output line 206 is reset by the pulse of the reset signal ΦVR2, the pulse of the read control signal Φv is given at a time T7, the signal electric charges of the respective sensor cells 201 are read to the output terminal O2. Thereafter, at a time T8, the sensor cell 201 is again reset by the pulse of the reset signal ΦVR1, and is ready for the X-ray input. The basic operation is repeated.

In this embodiment shown in FIG. 3, since the sources of a plurality of transistors 302 in the same column are connected to the output line 210 and the constant current source 211, a voltage appearing in the output line 210 becomes a value corresponding to the maximum voltage among the gate voltages of those transistors 302, but there arises no practical problem because the present invention is intended to measure the irradiation quantity for controlling the exposure quantity. The output line 210 and the constant current source 211 may be disposed for each of the transistors 302.

Figure 7:
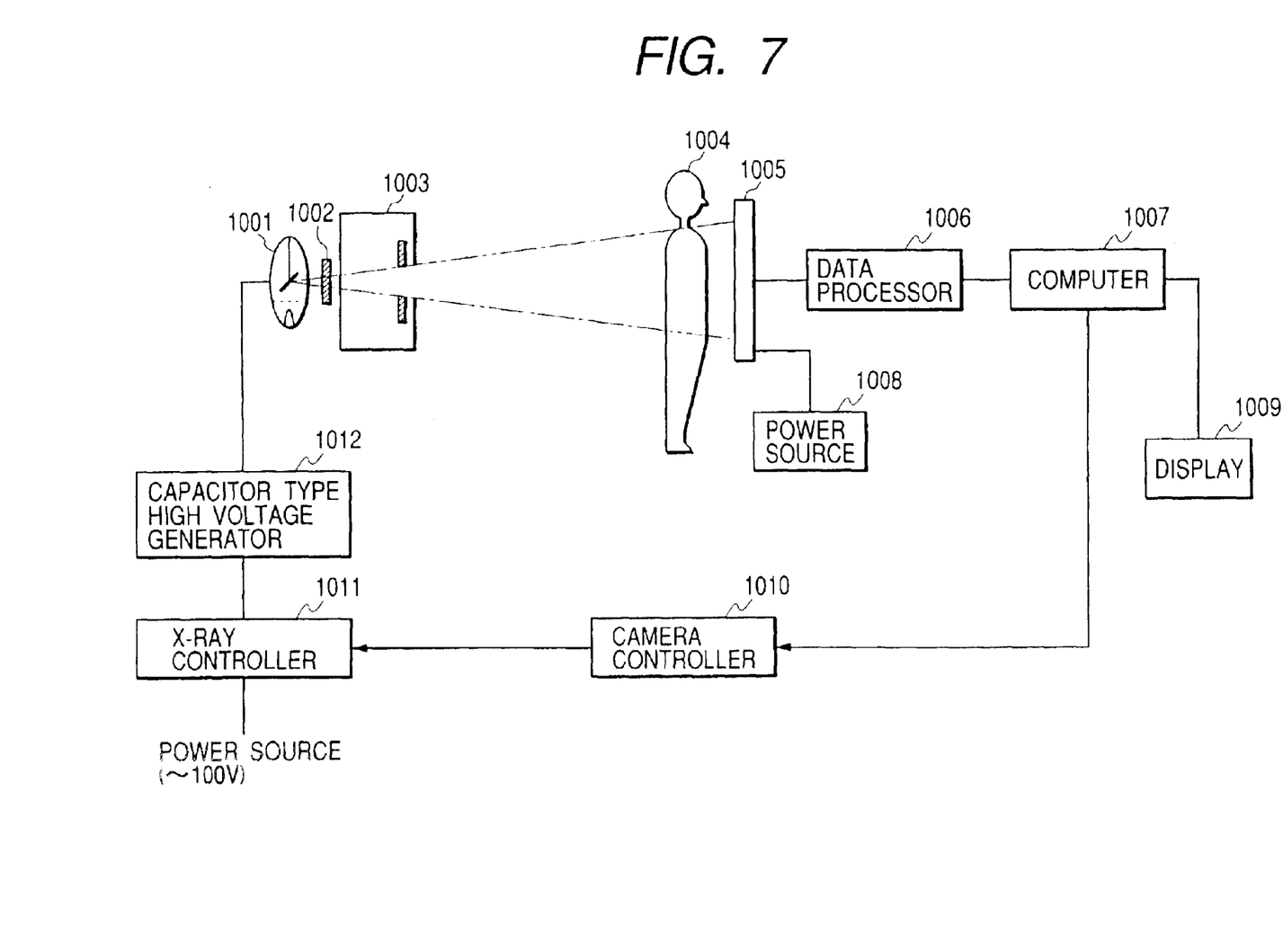
FIG. 7 is a conceptual diagram showing a medical applied system using the electromagnetic wave transforming device in accordance with the embodiment of the present invention.

FIG. 7 shows an example of a medical applied system.

Reference numeral 1005 denotes the above-mentioned electromagnetic wave transforming device which picks up an image of an object to be photographed 1004 and also detects the irradiation integral quantity of the X-ray that has passed through the object to be photographed 1004. The irradiation integral quantity is supplied to a computer 1007 through a data processing device 1006. The computer 1007 stops the irradiation of the X-ray by 1005 to the object to be photographed 1004 through a camera controller 1010 and an X-ray controller 1011, when the irradiation integral quantity becomes the predetermined value. In this way, the X-ray irradiation quantity to a human body which is the object to be photographed 1004 can be suppressed to the necessary quantity as small as possible.

Figure 8A:
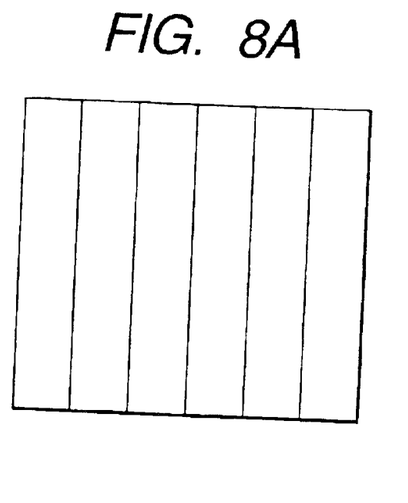
FIGS. 8A and 8B are diagrams showing a system of grouping an exposure quantity detection transistor in accordance with the first embodiment of the present invention.
Figure 8B:
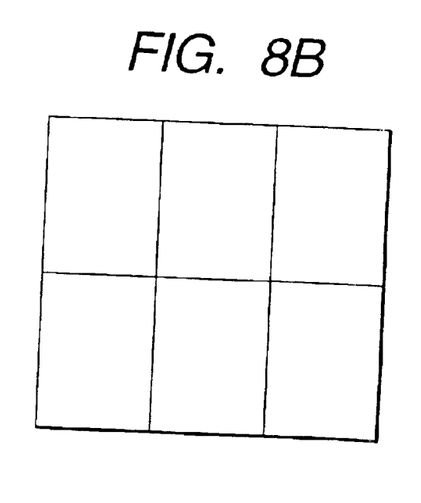

FIGS. 8A and 8B show a system of grouping the irradiation quantity detection due to the transistor 302. In an example shown in FIG. 3, there has been described that the transistor 302 is grouped for each of the columns. As another example, as shown in FIGS. 8A and 8B, the transistor 302 may be grouped so that a single output line 210 and a constant current source 211 are connected to the transistor 302 within the same group. The boundary of sections obtained by grouping the transistor 302 may or may not coincide with the boundary between the substrate 11 or the semiconductor substrate 12.

In the example shown in FIG. 8A, the photographing region is grouped into groups of 1 row x 6 columns arrangement. In the example shown in FIG. 8B, the photographing region is grouped into groups of 2 rows x 3 columns arrangement.

In the imaging region, for example, the sensor cells 201 of 2000×2000 are arranged, and in this case, in the example of FIG. 8A, the sensor cells 201 of 2000 (row direction)×333 to 334 (column direction) are contained in one group, and in the example of FIG. 8B, the sensor cells 201 of 1000 (row direction)×666 to 667 (column direction) are contained in one group. With this structure, the irradiation quantity of the X-rays can be detected at a plurality of portions.

Within each of the groups, a source voltage corresponding to the transistor 302 having the maximum gate voltage is obtained as a detected voltage. However, the detected voltage of which group among all of the groups is used is different depending on the imaging portions of the object to be photographed. That is, the detected voltage of an appropriately optimum group is used in accordance with a bust being imaged, a stomach being imaged, or the like among a human body which is an object to be photographed.

With the above structure, the X-ray imaging device and the X-ray irradiation quantity detecting circuit are integrated together to facilitate the downsizing of the device. Also, because the irradiation quantity of the X-rays is detected by the electromagnetic wave transforming device per se, it is possible to accurately detect the irradiation quantity. It is possible to detect the irradiation quantity of the X-rays without any influence on the picked-up image.

(Second Embodiment)

Figure 9:
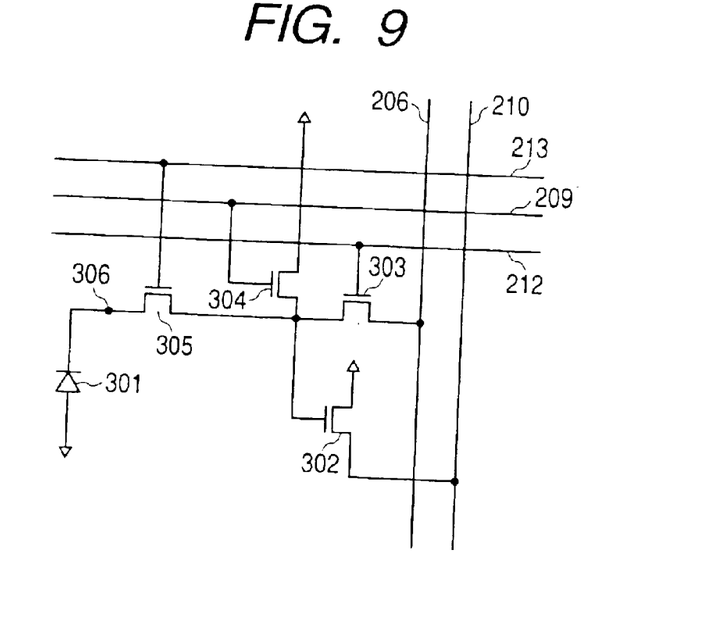
FIG. 9 is an equivalent circuit diagram showing the respective sensor cells in the electromagnetic wave transforming device in accordance with a second embodiment of the present invention.

FIG. 9 shows an equivalent circuit diagram of the respective sensor cells 201 in the electromagnetic transforming device according to a second embodiment.

A voltage clamp transistor 305 (hereinafter simply referred to as "transistor 305") is inserted between the X-ray sensing section 301 and the gate of the transistor 302. A constant potential is supplied to the wiring 213, thereby being capable of holding a potential of a point 306 which is connected with the transistor 305 at an opposite side of the high voltage supply side of the X-ray sensing section 301 constant. As a result, the applied electric field of the X-ray sensing section 301 can be held constant, thereby being capable of detecting a gain with respect to the X-rays without any change. It is important to hold the potential which is supplied to the wiring 213 constant.

(Third Embodiment)

Figure 10:
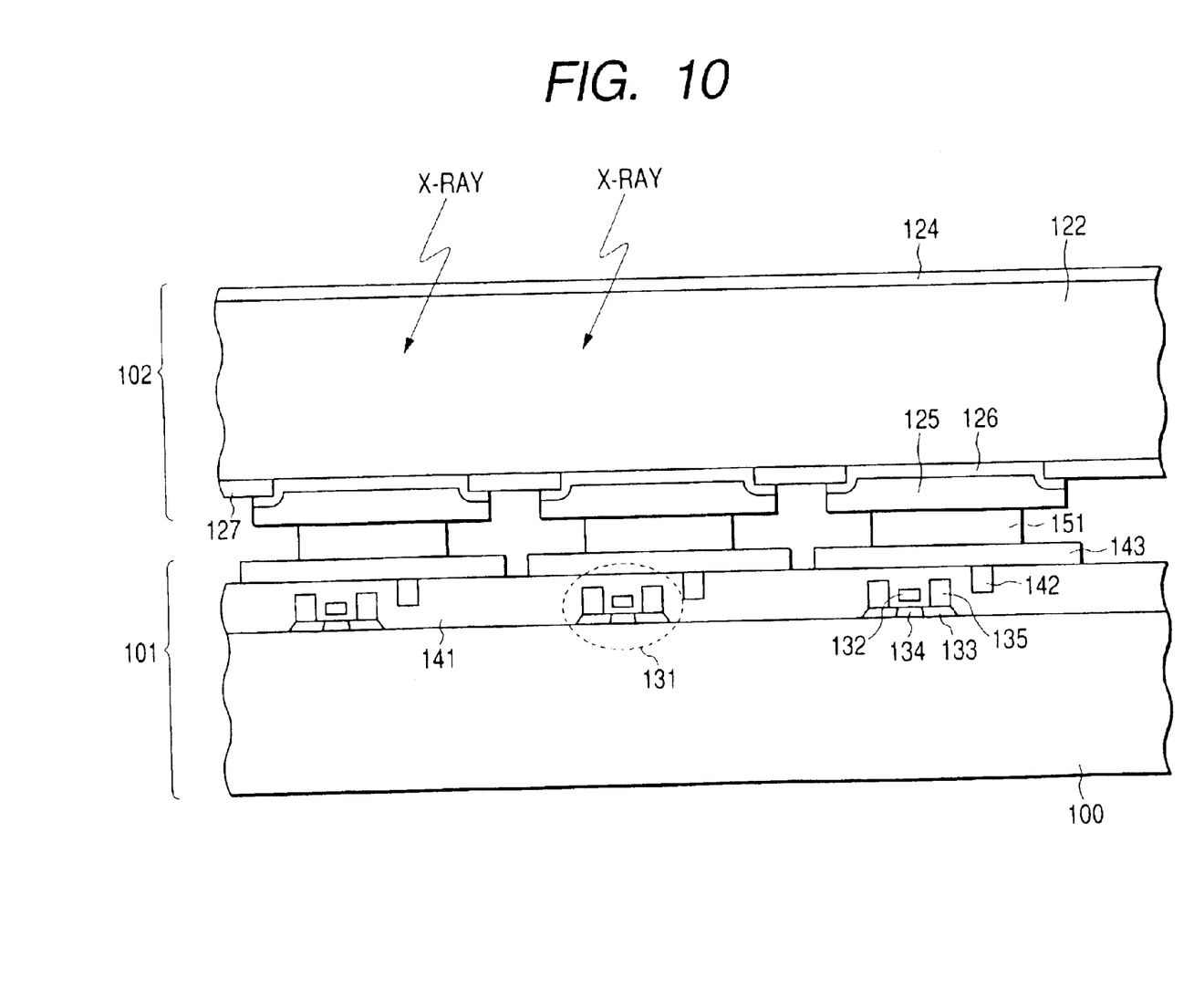
FIG. 10 is a partial cross-sectional view showing an electromagnetic wave transforming device in accordance with a third embodiment of the present invention.

FIG. 10 is a cross-sectional view showing an electromagnetic transforming device in accordance with a third embodiment. A difference of the electromagnetic transforming device shown in FIG. 10 from the electromagnetic transforming device according to the first embodiment shown in FIGS. 1A and 1B resides in that the p+ layer 123 and the n+ layer 121 are removed, and the metal layer 124 is made of, for example, AuGeNi. The metal layer 126 is made of, for example, AuGeNi as in the first embodiment.

In this structure, the radiant rays are detected not at a pn joint portion but in the semi-insulating (i layer) semiconductor substrate.

The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An electromagnetic wave detecting device, comprising:
   a plurality of sensor cells, each of which comprises:
   detecting means for transforming an electromagnetic wave into an electric charge for detection;
   storing means for storing a signal electric charge generated in said detecting means by the electromagnetic wave;
   reset means for resetting the signal electric charge of said storing means;
   first reading means for reading the signal electric charge; and
   second reading means for reading a potential of said storing means by the signal electric charge stored in said storing means in a nondestructive manner.

2. An electromagnetic wave detecting device according to claim 1, wherein said second reading means includes means for discriminating the potentials of the signal electric charges of a plurality of sensor cells to obtain a specific potential.

3. An electromagnetic wave detecting device according to claim 1, wherein said reset means, said storing means and said first and second reading means are formed of a thin film transistor formed on an insulating substrate, respectively.

4. An electromagnetic wave detecting device according to claim 3, wherein one terminal of said detecting means is connected with a potential supply means, and the other terminal of said detecting means is connected with a source or a drain of the transistors of said reset means and said reading means and a gate of the transistor of said storing means.

5. An electromagnetic wave detecting device according to claim 4, further comprising means for holding a voltage at the other terminal of said detecting means constant.

6. An electromagnetic wave detecting device according to claim 4, further comprising a source follower circuit that reads the gate potential of the transistor of said storing means to detect the stored electric charge.

7. An electromagnetic wave detecting device according to claim 3, wherein a semiconductor that forms the thin film transistor is made of non-single crystal silicon.

8. An electromagnetic wave detecting device according to claim 1, wherein said detecting means includes an X-ray sensing section in which a metal layer, an i layer and a metal layer are directly stacked one on another.

9. An electromagnetic wave detecting device according to claim 1, wherein said detecting means comprises a first substrate of semiconductor crystal that directly transforms the electromagnetic wave into the electric charge, said storing means, said reset means and said first reading means are formed on a second insulating substrate or a semiconductor substrate, the first substrate and the second substrate are stacked one on another, and a sensor cell of the first substrate and a reading circuit of the second substrate are electrically and mechanically connected to each other by a laminate structure of the first and second substrates.

10. An electromagnetic wave detecting system, comprising:
    detecting means for transforming an electromagnetic wave into an electric charge;
    reset means for resetting a potential of said detecting means;
    storing means for storing a signal electric charge generated in said detecting means by the electromagnetic wave;
    first reading means for reading the signal electric charge stored in said storing means;
    second reading means for reading a potential of the signal electric charge stored in said storing means in a nondestructive manner to detect an irradiation integral quantity of the electromagnetic wave; and
    control means for comparing the irradiation integral quantity with a predetermined value to stop the irradiation of the electromagnetic wave.

11. An electromagnetic wave detecting device, comprising:
    detecting means for transforming an electromagnetic wave into an electric charge for detection;
    storing means for storing a signal electric charge generated in said detecting means by the electromagnetic wave;
    a reset transistor for resetting the signal electric charge of said storing means;
    a first reading transistor for transferring the signal electric charge to a first signal line; and
    second reading transistor for reading a potential of said storing means by the signal electric charge stored in said storing means, wherein said second reading transistor has a terminal connected to a second signal line.

12. An electromagnetic wave detecting device according to claim 11, wherein said first and second transistors are made of non-single crystal silicon.

13. An electromagnetic wave detecting device, comprising:
    detecting means for transforming an electromagnetic wave into an electric charge for detection;
    storing means for storing a signal electric charge generated in said detecting means by the electromagnetic wave;
    a reset transistor for resetting the signal electric charge of said storing means;
    a first reading transistor for transferring the signal electric charge to an output circuit; and
    a second reading transistor for reading a potential of said storing means by the signal electric charge stored in said storing means, and transferring a signal based on the potential of said storing means to a circuit detecting irradiation quantity.

14. An electromagnetic wave detecting device according to claim 13, wherein said first and second transistors are made of non-single crystal silicon.

15. An electromagnetic wave detecting device according to claim 13, further comprising a circuit having an automatic exposure function by using an output from said circuit detecting irradiation quantity.

* * * * *